United States Patent
Berthod

(10) Patent No.: US 8,691,105 B2
(45) Date of Patent: Apr. 8, 2014

(54) METHOD OF DETECTING CONTAMINATION OF TITANIUM ALLOYS OF TWO-PHASE TYPE HAVING AN ALPHA AND A BETA PHASE

(75) Inventor: Gilles Berthod, Massy (FR)

(73) Assignee: SNECMA, Paris (FR)

( * ) Notice: Subject to any disclaimer, the term of this patent is extended or adjusted under 35 U.S.C. 154(b) by 153 days.

(21) Appl. No.: 13/392,112

(22) PCT Filed: Jul. 27, 2010

(86) PCT No.: PCT/FR2010/051583
§ 371 (c)(1),
(2), (4) Date: May 3, 2012

(87) PCT Pub. No.: WO2011/023874
PCT Pub. Date: Mar. 3, 2011

(65) Prior Publication Data
US 2012/0267527 A1    Oct. 25, 2012

(30) Foreign Application Priority Data
Aug. 28, 2009 (FR) .................................. 09 55866

(51) Int. Cl.
*B44C 1/22*      (2006.01)
(52) U.S. Cl.
USPC .................................. 216/83; 216/88; 216/89
(58) Field of Classification Search
USPC .................................. 216/83, 88, 89; 148/668
See application file for complete search history.

(56) References Cited

U.S. PATENT DOCUMENTS

| 4,551,434 A | 11/1985 | Thoma |
| 5,039,612 A | 8/1991 | Stacher |
| 5,413,649 A | 5/1995 | Dunand et al. |
| 8,500,929 B2 * | 8/2013 | Cotton et al. ............... 148/670 |
| 2005/0145508 A1 * | 7/2005 | Larsen et al. ............... 205/684 |
| 2007/0137734 A1 | 6/2007 | Pawar et al. |
| 2008/0289729 A1 | 11/2008 | Pawar et al. |
| 2009/0074836 A1 | 3/2009 | Pawar et al. |

OTHER PUBLICATIONS

International Search Report Issued Jan. 12, 2011 in PCT/FR10/51583 Filed Jul. 27, 2010.

* cited by examiner

*Primary Examiner* — Shamim Ahmed
(74) *Attorney, Agent, or Firm* — Oblon, Spivak, McClelland, Maier & Neustadt, L.L.P.

(57) ABSTRACT

A method of examining a titanium alloy with an alpha phase and a beta phase is disclosed. The method includes: cutting a sample of a part made of the alloy; preparing a region of the cut surface of the sample situated in the vicinity of the edge of the sample, the edge being in common with the outside surface of the part; observing the alpha phase of the region at a magnification of greater than ×5000; deciding on whether granularity is present or absent in the alpha phase of a first zone contiguous with the edge of the sample; and concluding that the alloy has been contaminated with a gas if granularity is found to be absent in the alpha phase of the contiguous zone whereas granularity is present in the alpha phase outside the contiguous zone.

20 Claims, 6 Drawing Sheets

METHOD OF DETECTING CONTAMINATION OF TITANIUM ALLOYS OF TWO-PHASE TYPE HAVING AN ALPHA AND A BETA PHASE

The present invention relates to a method of examining a titanium alloy of two-phase type having an alpha phase and a beta phase.

The alpha phase is one of the phases present in most alloys of titanium (Ti), and it corresponds to a compact hexagonal crystal lattice of Ti atoms.

Titanium alloys that include an alpha phase are easily contaminated by other chemical elements with which they come into contact. For example, they are contaminated by gases (such as oxygen, nitrogen, hydrogen, halogens). For reasons of reaction kinetics, such contamination is usually visible when the material has been exposed to a temperature in the vicinity of 500° C. or more. Such contamination leads to the titanium alloy being embrittled from its exposed surface, which leads to a deterioration in its mechanical characteristics.

That is why the heat treatments to which a titanium alloy is subjected during fabrication are performed in a vacuum, i.e. with exposure to gas that is sufficiently low for the surface of the titanium alloy not to be contaminated.

In spite of such precautions, surface contamination of the alloy can occur. It is therefore essential to verify the presence or absence of contamination. Several techniques are presently in use for detecting surface contamination.

A first detection technique comprises chemically analyzing the alloy. In known manner, that chemical analysis is performed by means of a microprobe. That technique is onerous and not very reliable, and it is qualitative (it does give a measure of the extent of the contamination).

A second technique is mechanical testing. By way of example, and in known manner, a notched traction test piece made of the alloy is tested to breakage. That technique is onerous, unreliable, and qualitative. Alternatively, and in known manner, it is possible to use a fine sheet of the alloy, which sheet is folded until cracks appear. That technique is qualitative only.

A third technique comprises examining the microstructure of the titanium alloy. The steps of that known technique are shown diagrammatically in FIG. 5. A sample of a part made of the alloy is cut (step a)) so that the surface of the cut 2 leads to the outside surface 1 of the part. A region 4 of the surface of the cut 2 is then polished, said region 4 being situated in the vicinity of the edge 50 of the sample, the edge 50 being in common with the outside surface 1 of the part, and thereafter the following are applied in succession to said region 4: a first chemical reagent; and then a second chemical reagent (step b)). These chemical etches using reagents serve to reveal the microstructure of the alloy. The edge of the sample is then observed in an optical microscope in order to detect the presence or the absence therein of a white margin 10 (step c)).

FIG. 6 is a photomicrograph at a magnification of ×500 from an optical microscope, showing a cut surface of a piece of TA6Zr4DE titanium alloy that has been contaminated with oxygen. The presence of a white margin 10 can be seen along the edge 50 of the sample. It is known that such a white margin 10 is a sign that the alloy has been contaminated by gases from its surface. The depth of the contamination is given by the width of this white margin 10.

Nevertheless, that technique of metallographic examination sometimes remains relatively inaccurate. Both the varying grain size and detecting contamination in a manner that is based solely on visually assessing contrast between the white margin and the adjacent darker gray portions, prevent an accurate measurement being made of the thickness of the white margin, so that technique does not always make it possible to know exactly the extent of the contamination.

Furthermore, that technique is not applicable to certain titanium alloys, such as TA5CD4. Thus, FIG. 2 is a photomicrograph from an optical microscope showing a cut surface of a TA5CD4 titanium alloy that has been contaminated with oxygen, and no white margin can be seen along the edge 50 of the sample.

The present invention seeks to remedy those drawbacks.

The invention seeks to provide a method that makes it possible to determine whether a titanium alloy has been contaminated by foreign gaseous chemical elements, which method is applicable to all titanium alloys of two-phase type with an alpha phase and a beta phase, and enables the contamination to be measured more accurately.

This object is achieved by the fact that the method comprises the following steps:
  a) cutting a sample of a part made of said alloy;
  b) preparing a region of the cut surface of the sample that is situated in the vicinity of the edge of the sample, the edge being in common with the outside surface of the part, so as to enable the region to be observed;
  c) observing the alpha phase of the region at a magnification of greater than ×5000;
  d) deciding on whether granularity is present or absent in the alpha phase of a first zone contiguous with the edge of the sample; and
  e) concluding that the alloy has been contaminated with a gas if granularity is found to be absent in the alpha phase of the contiguous zone whereas granularity is present in the alpha phase outside the contiguous zone.

By means of these provisions, it is possible to determine reliably whether a titanium alloy of two-phase type with an alpha phase and a beta phase has been contaminated by foreign gaseous chemical elements, and regardless of the titanium alloy. Furthermore, the greater magnification at which the observation is performed makes it possible to make an accurate measurement of the contamination, since the boundary between a zone without granularity and a zone with granularity is thus well defined.

Advantageously, the preparation of the region of the titanium alloy sample comprises polishing said region and then chemically etching the region with a single reagent.

It is thus no longer necessary to use two reagents in order to prepare the surface of the titanium alloy sample. The examination of a sample is thus made simpler and more reliable.

The invention can be well understood and its advantages appear better on reading the following detailed description of an implementation given by way of non-limiting example. The description refers to the accompanying drawings, in which.

Until now, when observing a part made of titanium alloy of two-phase type with an alpha phase and a beta phase, if no white margin could be seen along the edge of the sample in common with the surface of said part, then it was concluded that the part had not been contaminated. Thus, if the mechanical performance of the part was found to be unsatisfactory, it was concluded that the poor performance was the result, for example, of a fabrication defect, of a poor surface state, of work hardening, or of poor operating conditions. Any of those events might explain poor mechanical performance.

The inventors have collected a large number of samples of various titanium alloys of two-phase type with an alpha phase and a beta phase, and in non-obvious manner they have considered observing the samples at a magnification that is much greater than the usual magnification of about ×500, which suffices for observing the white margin of alloys that have been contaminated at the surface by gaseous elements. Thus, using a magnification greater than or equal to ×5000, the inventors have observed, unexpectedly, that certain zones of the alpha phase do not present granularity, whereas other zones of the alpha phase do present granularity.

Figure 1:
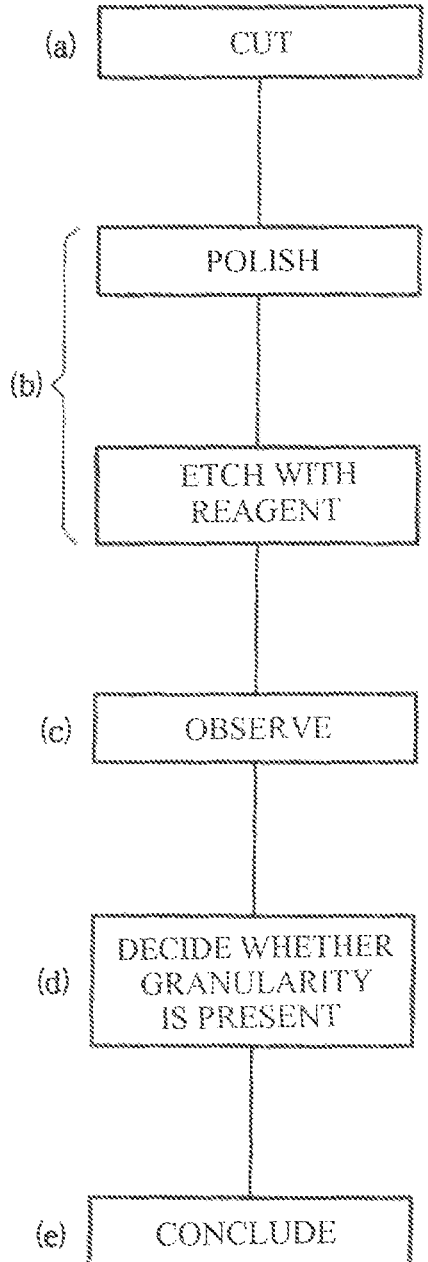
FIG. 1 is a diagrammatic representation of the steps of the method of the invention.
Figure 1:
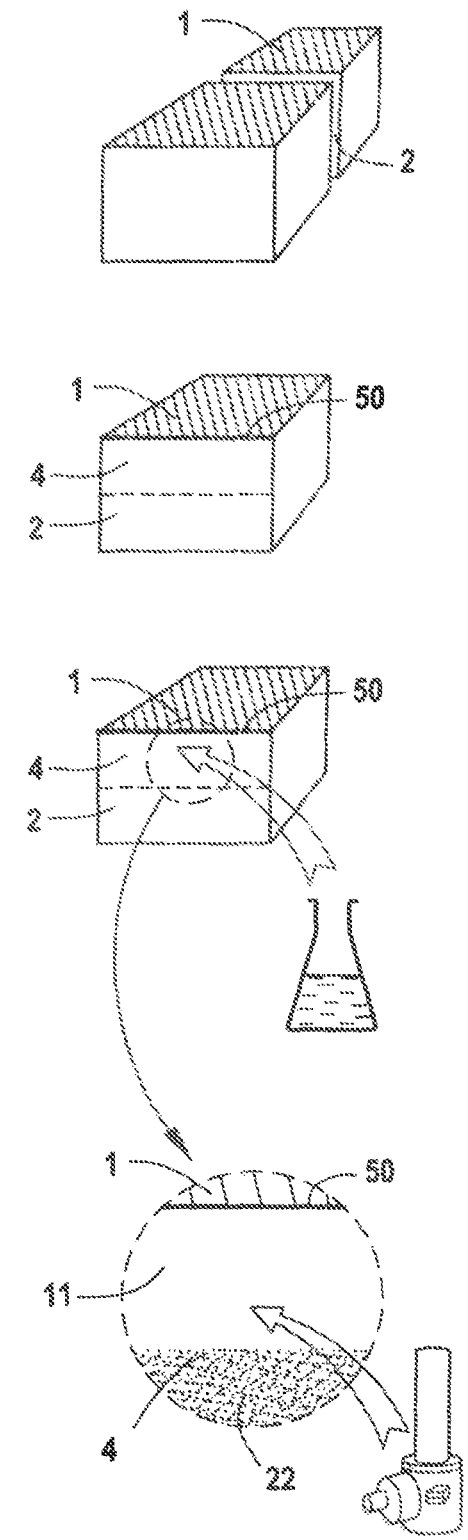

FIG. 1 is a diagrammatic representation of the steps of the method of the invention that makes it possible to observe the granularity.

Firstly, a sample of a part made of titanium alloy of two-phase type having an alpha phase and a beta phase is cut (step a)) such that the surface of the cut 2 leads to the outside surface 1 of the part.

Thereafter, a region 4 of the surface of the cut 2 is prepared, said region 4 being situated in the vicinity of the edge 50 of the sample (step b)), this edge 50 being in common with the outside surface 1 of the part. The purpose of this preparation is to enable the region 4 to be observed.

For example, this preparation comprises polishing the region 4 and then chemically etching the region 4 with a single reagent. Unlike the prior art method in which it is necessary to use two reagents in succession, and for different durations, in the method of the invention it is possible to use a single reagent. This simplifies the method and attenuates any risk of poor preparation.

For example the polishing is specular polishing.

For example, the reagent is an aqueous solution of hydrofluoric acid HF at 0.5%. This reagent is applied to the surface of the sample for a duration lying in the range 15 seconds (s) to 30 s.

Alternatively, it is possible to use more than one reagent.

Thereafter, the alpha phase of the region is observed at a magnification of at least ×5000 (step c)).

These observations are performed using a scanning electron microscope (SEM).

Alternatively, these observations may be performed using some other microscope that is capable of magnifying by more than ×5000. Nevertheless, these observations cannot be performed with a current optical microscope since the maximum magnification thereof is about one thousand times.

By way of example, the magnification used is greater than ×10,000.

It is then decided whether or not granularity is present in the alpha phase of the zone 11 that is contiguous with the edge of the sample (step d)).

Thereafter, it is concluded that the alloy has been contaminated by a gas if an absence of granularity is found in the alpha phase of said contiguous zone 11, while granularity 22 is present in the alpha phase outside said contiguous zone 11 (step e)).

Figure 6:
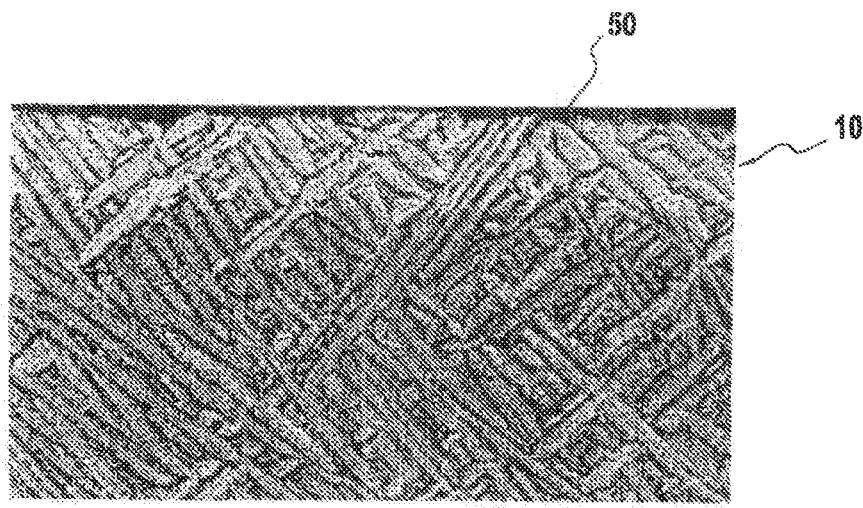
FIG. 6 is a photomicrograph from an optical microscope of a cut surface of a TA6Zr4DE titanium alloy contaminated with oxygen, shown at a magnification of ×500.
Figure 7:
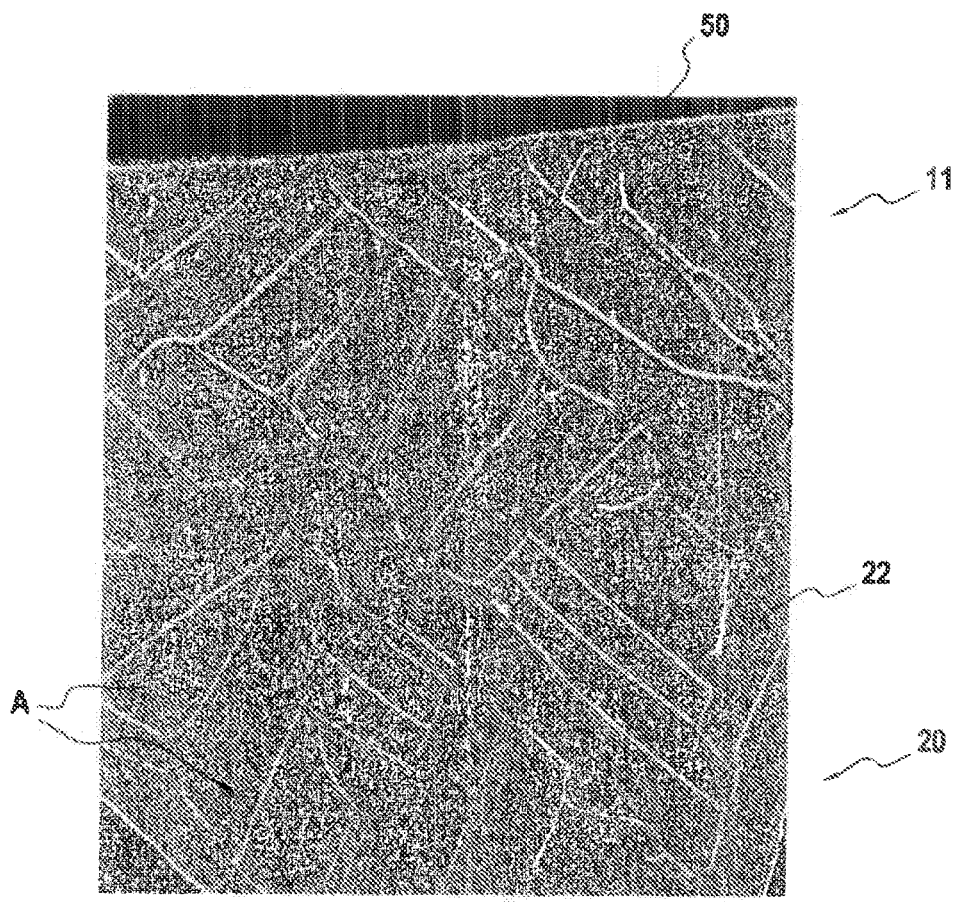
FIG. 7 is a photomicrograph from a scanning electron microscope of the cut surface of the FIG. 6 TA6Zr4DE titanium alloy at a greater magnification.

Thus, as shown in FIG. 7, which is an SEM photomicrograph at a magnification of ×5000 of the cut surface of a TA6Zr4DE titanium alloy sample that has been contaminated with oxygen (with the optical microscope photomicrograph thereof also being shown in FIG. 6), it can be seen that in a first zone 11 contiguous with the edge 50 of the sample, the alpha phase A does not include granularity, whereas in a second zone 20 further away from the edge 50, granularity 22 is indeed present within the alpha phase A.

Thus, the inventors have observed that an absence of granularity in the contiguous first zone 11, which absence corresponds to the white margin 10 observed in FIG. 6.

Figure 8:
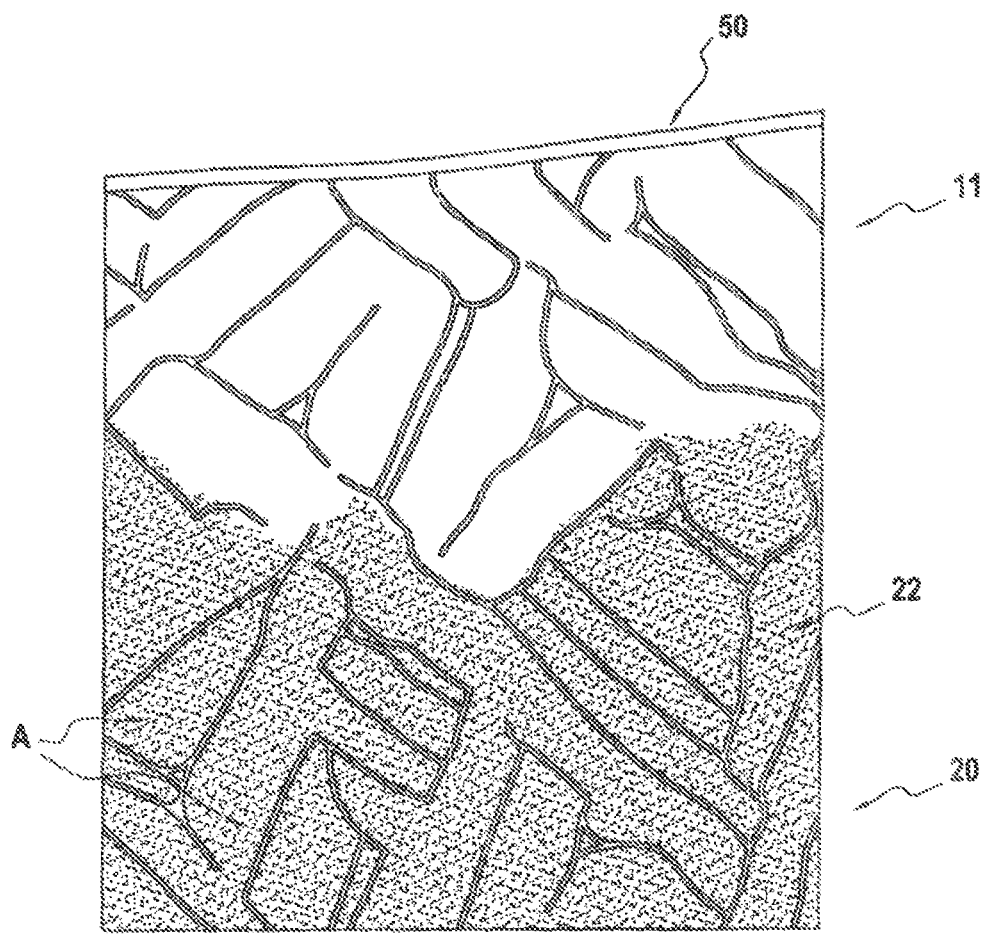
FIG. 8 is a diagrammatic representation of the microstructure shown in FIG. 7.

FIG. 8 is a diagram showing the structure observed in FIG. 7.

In order to confirm the hypothesis whereby the absence of granularity 22 in the alpha phase of the zone 11 contiguous to the edge of the sample is correlated with contamination (of said contiguous zone 11) of said sample by means of a gas, the inventors have observed the edges of TA6Zr4DE titanium alloys that are not contaminated but that have been subjected to surface modification (e.g. work hardening, polishing). The inventors have found that the presence of granularity 22 in the alpha phase of the zone 11 contiguous with the edge 50 of a part made of one of these alloys, thereby validating the above hypothesis.

Figure 2:
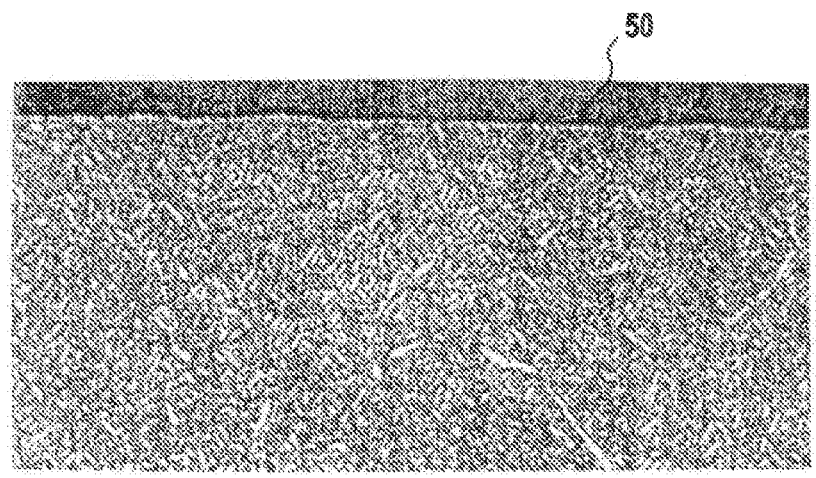
FIG. 2 is a photomicrograph from an optical microscope showing a cut surface of a TA5CD4 titanium alloy that has been contaminated with oxygen.
Figure 3:
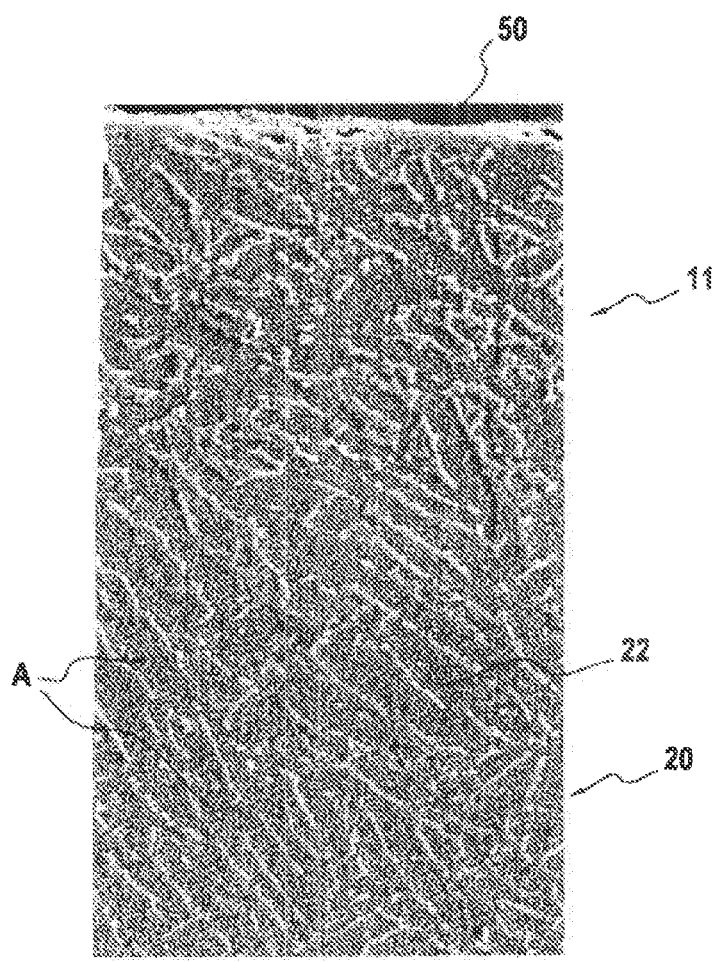
FIG. 3 is a photomicrograph from a scanning electron microscope of the cut surface of the FIG. 2 TA5CD4 titanium alloy at a greater magnification.

Advantageously, the method of the invention makes it possible to determine whether a TA5CD4 titanium alloy has or has not been contaminated at the surface, whereas that information is not available using a prior art observation method. Thus, FIG. 3 is an SEB photomicrograph at a magnification of ×5000 of the cut surface of the TA5CD4 titanium alloy for which an optical microscope photomicrograph is also shown in FIG. 2. It can be seen that in a first zone 11 contiguous with the edge 50 of the sample, the alpha phase A does not have granularity, whereas in a second zone 20 further away from the edge 50 (i.e. a zone that is outside the contiguous zone 11), granularity 22 is present within the alpha phase A.

Figure 4:
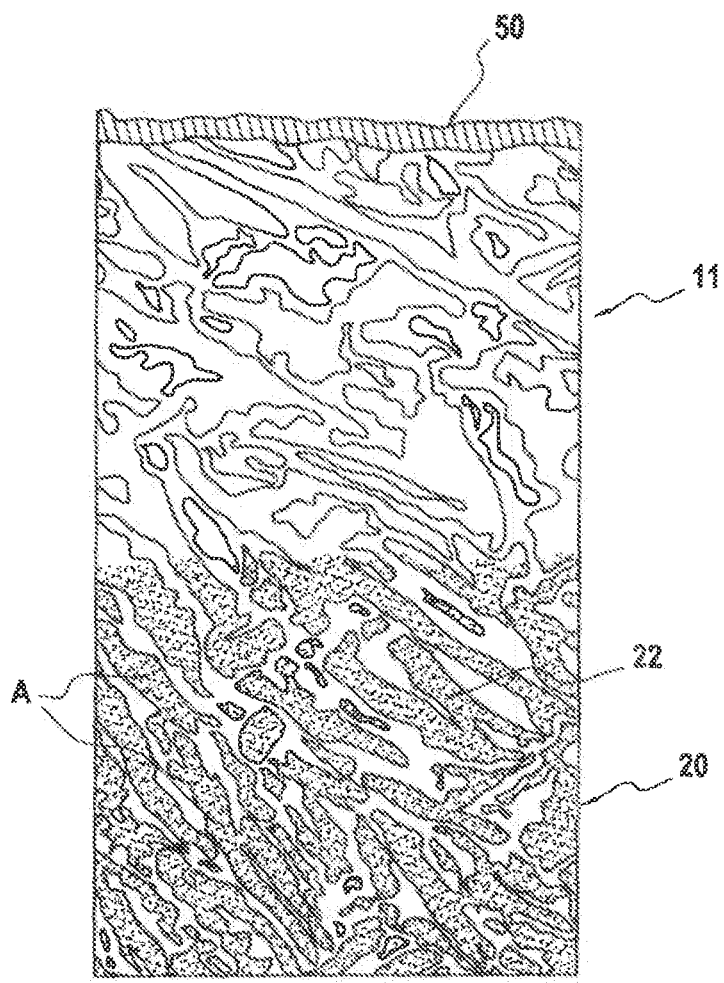
FIG. 4 is a diagrammatic representation of the microstructure shown in FIG. 3.
Figure 5:
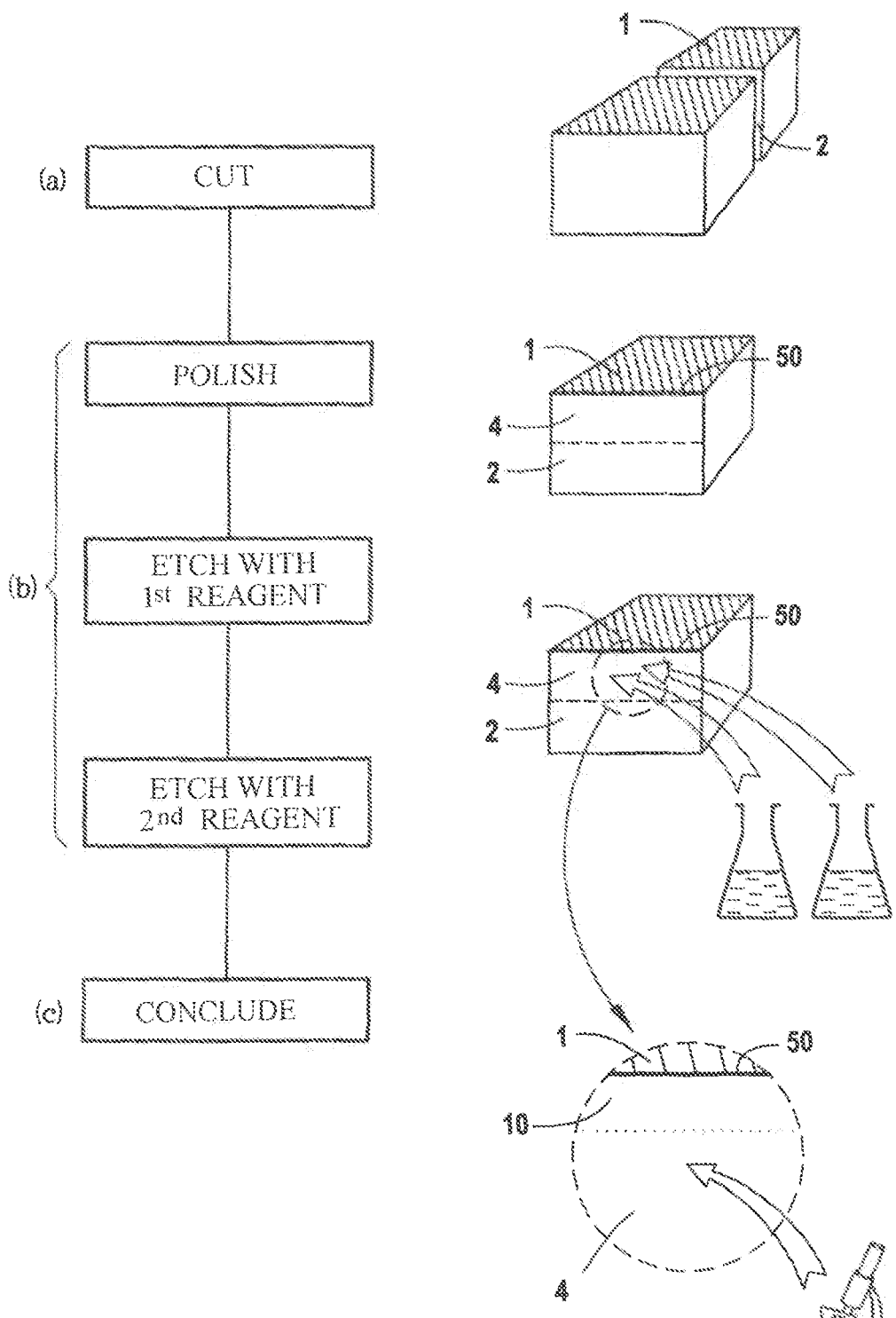
FIG. 5 is a diagrammatic representation of the steps of the prior art method of examining the microstructure of a titanium alloy.

FIG. 4 is a diagram showing the structure observed in FIG. 3.

The invention claimed is:

1. A method of examining a titanium alloy, the method comprising:
   a) cutting a sample of a part comprising a titanium alloy of two-phase, having an alpha phase and a beta phase, to obtain a cut surface;
   b) preparing a region of the cut surface that is located in a vicinity of an edge of the sample, the edge being in common with an outside surface of the part;
   c) observing the alpha phase of the region at a magnification of greater than ×5000;
   d) deciding whether granularity is present or absent in the alpha phase of a first zone contiguous with the edge of the sample; and
   e) concluding that the alloy has been contaminated with a gas if granularity is absent in the alpha phase of the first zone and granularity is present in the alpha phase outside the first zone.

2. The method of claim 1, wherein the observing is performed with a scanning electron microscope.

3. The method of claim 1, wherein the preparing comprises polishing the region and then chemically etching the region with at least one reagent.

4. The method of claim 3, wherein the chemical etching is performed using a single reagent.

5. The method of claim 4, wherein the reagent is a 0.5% aqueous solution of hydrofluoric acid.

6. The method of claim 2, wherein the preparing comprises polishing the region and then chemically etching the region with at least one reagent.

7. The method of claim 6, wherein the chemical etching is performed using a single reagent.

8. The method of claim 7, wherein the reagent is a 0.5% aqueous solution of hydrofluoric acid.

9. The method of claim 3, wherein the polishing is specular polishing.

10. The method of claim 6, wherein the polishing is specular polishing.

11. The method of claim 3, wherein the at least one reagent comprises a 0.5% aqueous solution of hydrofluoric acid.

12. The method of claim 6, wherein the at least one reagent comprises a 0.5% aqueous solution of hydrofluoric acid.

13. The method of claim 3, wherein the chemical etching is performed for a duration of 15 to 30 seconds.

14. The method of claim 6, wherein the chemical etching is performed for a duration of 15 to 30 seconds.

15. The method of claim 5, wherein the chemical etching is performed for a duration of 15 to 30 seconds.

16. The method of claim 8, wherein the chemical etching is performed for a duration of 15 to 30 seconds.

17. The method of claim 1, wherein the observing is at a magnification of greater than ×10,000.

18. The method of claim 2, wherein the observing is at a magnification of greater than ×10,000.

19. The method of claim 5, wherein the observing is at a magnification of greater than ×10,000.

20. The method of claim 8, wherein the observing is at a magnification of greater than ×10,000.

* * * * *